United States Patent [19]

McCoy

[11] Patent Number: 4,601,705
[45] Date of Patent: Jul. 22, 1986

[54] STEERABLE AND AIMABLE CATHETER

[76] Inventor: William C. McCoy, 11339 Valley Meadow Dr., Zionsville, Ind. 46077

[21] Appl. No.: 728,634

[22] Filed: May 3, 1985

Related U.S. Application Data

[63] Continuation-in-part of Ser. No. 547,402, Oct. 31, 1983, Pat. No. 4,543,090.

[51] Int. Cl.⁴ ............................................. A61M 25/00
[52] U.S. Cl. ........................................ 604/95; 128/657
[58] Field of Search ................... 604/95, 264, 280, 281; 128/6, 657

[56] References Cited

U.S. PATENT DOCUMENTS

| | | |
|---|---|---|
| 3,043,309 | 7/1962 | McCarthy . |
| 3,605,725 | 9/1971 | Bentov . |
| 3,674,014 | 7/1974 | Tillander . |
| 3,729,008 | 4/1973 | Berkovits . |
| 3,773,034 | 11/1973 | Burns et al. . |
| 3,890,977 | 6/1975 | Wilson . |
| 4,146,019 | 3/1979 | Bass et al. . |
| 4,176,662 | 12/1979 | Frazer . |

Primary Examiner—Stephen C. Pellegrino
Assistant Examiner—Jerome R. Smith, Jr.
Attorney, Agent, or Firm—Barnes & Thornburg

[57] ABSTRACT

A catheter or the like is steerable through cavities within a body and aimable toward organs or tissue within the body. The catheter includes an elongated tubular member having a proximal end and a distal end for insertion into the body, a plurality of temperature-activated memory elements in the distal end of the tubular member, and a core for supporting the memory elements. Each memory element assumes a preset shape when heated to a predetermined temperature. A sleeve is provided to couple slidably each memory element to the core so that each memory element is permitted to slip in relation to the core and also to couple each memory element so that movement of one element results in movement of the other elements. Each memory element is moved to another shape when the memory element coupled thereto is heated to the predetermined temperature. A control system adjacent the proximal end of the tubular member allows an operator to control selectively the temperature of each temperature-activated element to deflect the distal end of the tubular member so as to either direct the course of the tubular member or to direct the distal end of the tubular member toward an organ or tissue within the body.

15 Claims, 11 Drawing Figures

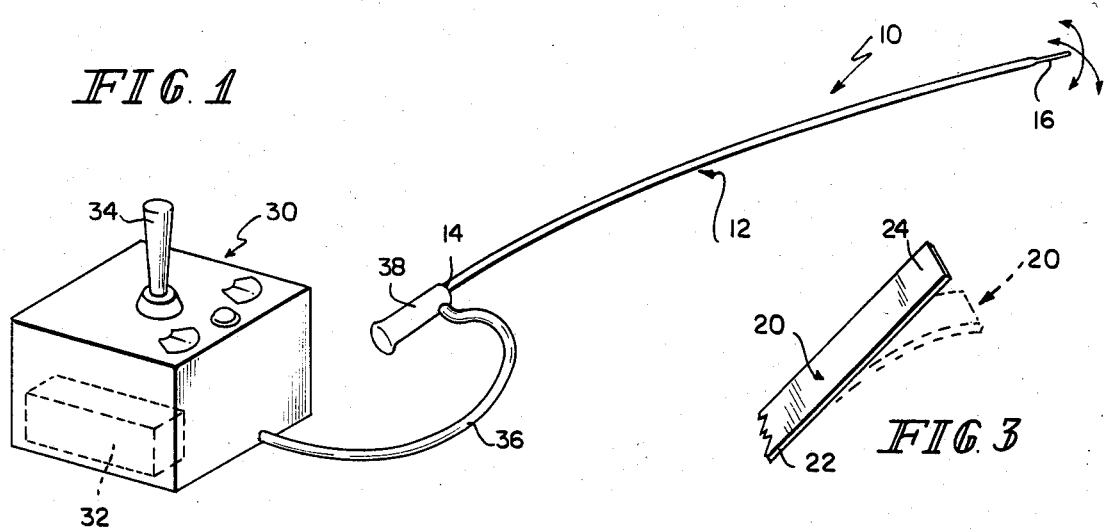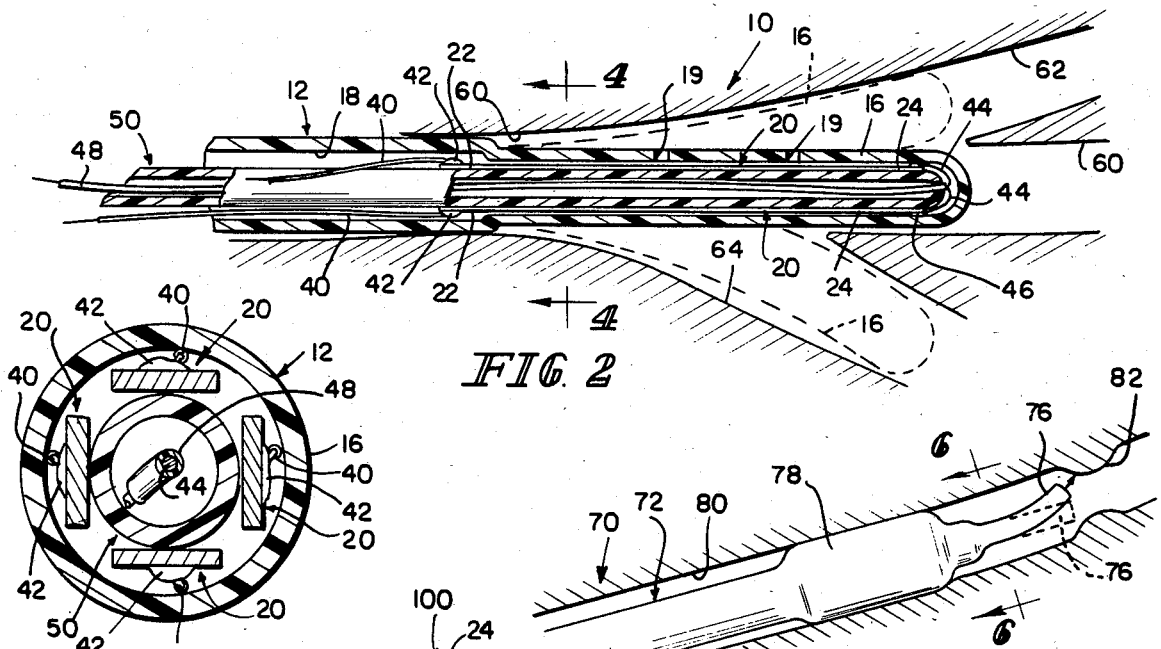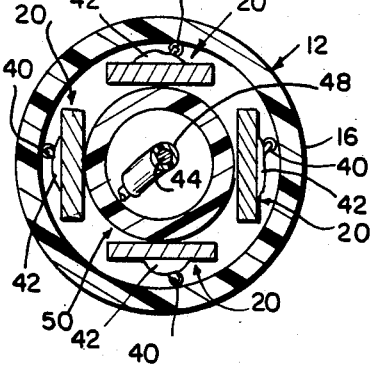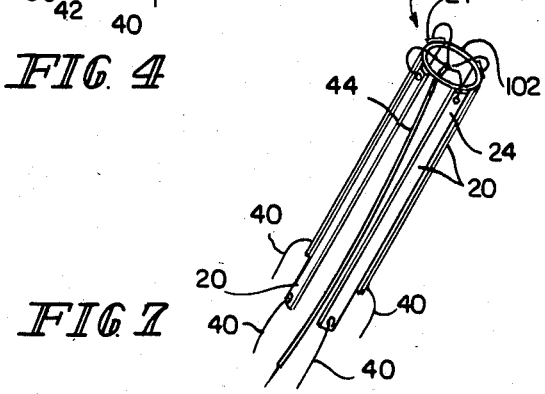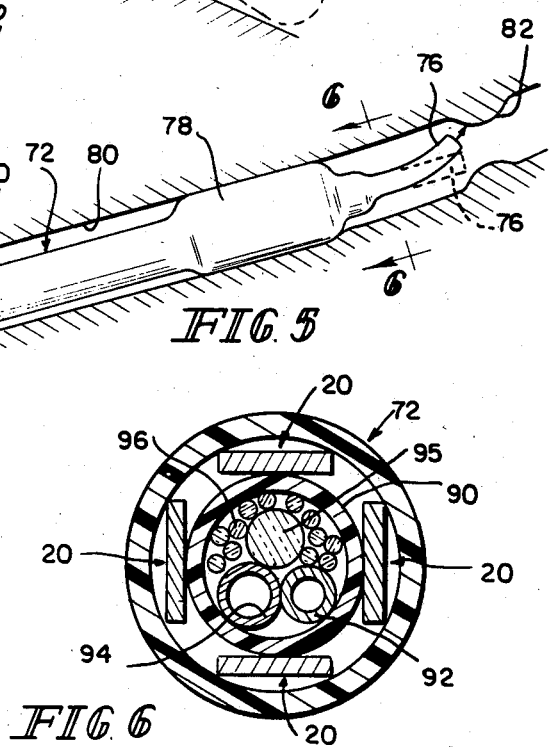

STEERABLE AND AIMABLE CATHETER

This application is a continuation-in-part of copending application Ser. No. 06/547,402 filed Oct. 31, 1983, now U.S. Pat. No. 4,543,090.

The present application relates to catheters, cannulae, and the like and particularly to catheters that are steerable through body cavities and aimable at obstructions, organs, or tissue within the body from a position external to the body.

Some attempts have been made in the past to provide catheters having distal ends which, when inserted into a body, are manipulatable to advance the catheter through body cavities. See for example, U.S. Pat. Nos. 3,674,014 and 3,773,034. The catheter disclosed in U.S. Pat. No. 3,674,014 includes permanent magnets and employs a magnetic field to bend the distal end of the catheter. The catheter disclosed in U.S. Pat. No. 3,773,034 includes fluid conduits and employs a fluid to bend the distal end of the catheter. Other controlled devices are disclosed in U.S. Pat. Nos. 3,605,725 and 4,176,662. However, these prior devices are quite difficult to control and manipulate.

Some work has previously been done to produce a catheter which is readily insertable while being effectively anchorable in a body cavity. See, for example, U.S. Pat. Nos. 3,729,008 and 3,890,977. In U.S. Pat. No. 3,890,977 the distal end of the catheter is formed into a desired shape by using a material exhibiting mechanical memory that is triggered by heat. By heating the mechanical memory material, the distal end of the catheter is shaped to anchor the catheter within the body. However, the change of the shape of the distal end in these prior devices is limited to a single direction.

Other devices are known for guiding a catheter to a particular location within the body. See for example U.S. Pat. No. 3,043,309.

One object of the present invention is to provide a steerable catheter, cannula, and the like which is easy to operate and steerable in a plurality of different directions within the body.

Another object of the present invention is to provide an aimable catheter, cannula, and the like which is easy to operate and which can be aimed at obstructions, organs, or tissues in a plurality of different directions within the body.

Yet another object of the present invention is to provide a catheter of improved maneuverability having means for slidably coupling each of a plurality of temperature-activated memory elements to a core member so that each memory element is permitted to slip in relation to the adjacent core member when at least one of the memory elements is heated to assume a predetermined "memorized" shape.

According to the present invention, a catheter includes a tubular member having a distal end for ready insertion into a body, a core member within the distal end of the hollow tubular member and movable therein, and a plurality of temperature-activated memory elements in the distal end, each memory element assuming a predetermined shape when heated to a predetermined temperature. A sleeve is provided for coupling each memory element to a distal end of the core member so that each memory element is permitted to slip in relation to the adjacent core member when at least one of the memory elements moves to assume its predetermined shape. Control means is provided for heating selectively each memory element. The control means is operable to heat at least one of the memory elements so that it moves to assume its predetermined shape for the purpose of deflecting the distal end of the tubular member in a selected direction. The assistive sleeve permits each memory element to slide in relation to the adjacent core member during operation of the control means. Thus, the memory elements are able to slip in relation to the distal end of the core member so that maneuverability of the tubular member within the body toward a selected deflected position is increased.

In preferred embodiments of the present invention, each memory element includes a forward tip portion positioned in close proximity to the distal end of the core member and slidably coupled thereto by the sleeve, and a remaining body portion. Further, wrap means is provided for slidably coupling at least a segment of the body portion of the memory element to the core member so that the remaining body portion segment is permitted to slip in relation to the adjacent core member along with the tip portion. Desirably, the wrap is a continous filament embracing a radially outwardly-facing surface of each of the memory elements in sufficiently tight relation to retain the memory elements in their coupled position while permitting relative slipping movement between each coupled memory element and the core member. In this way, the steerability and aimability of the catheter of the present invention is improved since the problem of restricted catheter movement caused by an inflexible, unbending, rigid connection between the memory elements and the core member, is solved, in part, due to provision of means for slidably coupling the memory elements to the core member.

Various other features and advantages of the present invention will become apparent in view of the following detailed description of embodiments thereof representing the best mode of carrying out the invention as presently perceived, which description should be considered in conjunction with the accompanying drawings, in which:

FIG. 1 is a perspective view of a steerable and aimable catheter, cannula, and the like embodying the present invention;

FIG. 2 is a longitudinal cross-sectional view, partly broken away, of a body cavity and the distal end of the catheter, cannula, and the like shown in FIG. 1;

FIG. 3 is a perspective view of an embodiment of a temperature-activated memory element employed in the catheter, cannula, and the like showing its different shapes;

FIG. 4 is a transverse cross-sectional view of the distal end of the catheter, cannula, and the like embodying the present invention taken generally along section lines 4—4 in FIG. 2;

FIG. 5 is a longitudinal cross-sectional view of a body cavity showing the aimable feature of a catheter, cannula, and the like embodying the present invention;

FIG. 6 is a transverse cross-sectional view of the embodiment of the catheter, cannula, and the like shown in FIG. 5 taken generally along section lines 6—6 of FIG. 5;

FIG. 7 is a perspective view of an embodiment of a plurality of temperature-activated memory elements employed in the distal end of the catheter, cannula, and the like to deflect or move the distal end for steering and aiming thereof;

Figure 8:
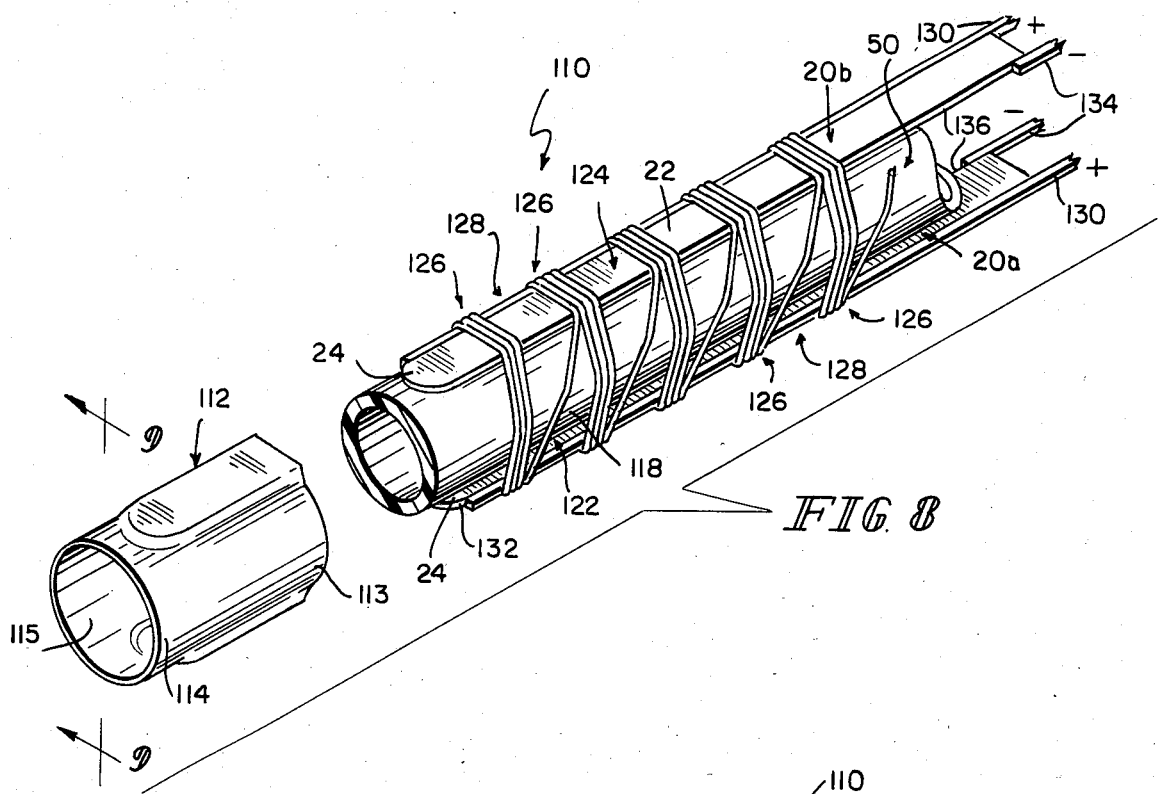
FIG. 8 is an exploded view of another embodiment of the present invention.

A catheter 10 embodying the present invention is shown generally in FIG. 1. Catheter 10 includes an elongated tubular member 12 having a proximal end 14 and a steerable and aimable distal end 16. In the illustrative embodiment, the tubular member 12 is formed of plastic, TEFLON, or cross-linked kynar or polyethylene. As will become apparent in the description of catheter 10, it is desirable that tubular member 12 be formed of a material that is flexible, that can withstand heat, and which provides electrical insulation.

As best shown in FIG. 2, the tubular member 12 can have a lumen 18 for the passage of fluid from the proximal end 14 to the distal end 16 and vice versa. Typically, the tubular member 12 includes one or more holes or openings 19 through which fluids are either injected into or drained from a body cavity. Some cannulae may have an open distal end 16 for insertion and withdrawal of medical instruments.

As shown in FIGS. 2 and 3, a plurality of temperature-activated memory elements 20 are incorporated into the distal end 16 of the tubular member 12. It may be desirable to isolate the memory elements 20 from the body cavity. The temperature-activated memory elements 20 preferably exhibit a memory characteristic in response to temperature changes. The elements 20 may be wires or flat strips such as shown in FIG. 3. In the illustrative embodiment, the temperature-activated memory elements 20 are formed of a mechanical memory metal such as a nickel titanium alloy. While a nickel titanium alloy is desirable, other metal elements having a memory characteristic related to temperature could be used without departing from the scope of the invention. Such metal elements should have a high resistance to electric current so that heat is produced when current is passed therethrough.

As shown in FIG. 3, the elements 20 have a body portion 22 and a tip portion 24. Each element 20 has a first or preset shape represented by the broken lines in FIG. 3 and a second shape represented by the solid lines in FIG. 3. Illustratively, the preset shape is an arcuate shape, and the second shape is a straight shape. It will be appreciated that the preset shape could be any shape.

Each temperature-activated memory element 20 is originally annealed into its preset shape (represented by the broken lines in FIG. 3). Memory elements 20 are cooled and straightened to their second shape (represented by the solid lines in FIG. 3) before incorporation into the distal end 16 of the tubular member 12. When the elements 20 are again heated to a predetermined transitional temperature they return to their preset shape. By applying an opposing force to an element 20 that has moved to assume its preset shape it can be moved to its second shape (represented by the solid lines in FIG. 3). In the illustrative embodiment, the predetermined transitional temperature is any temperature above body temperature. For example, the predetermined transitional temperature may be in the range of 100° to 150° F.

The memory elements 20 can either be directly incorporated into the distal end 16 of the tubular member 12 or can be carried on an electrically insulative core 50. As will be discussed later, each memory element 20 must be coupled to at least one other memory element 20 so that when one of the memory elements is heated it applies a force to move the other memory element 20.

The catheter 10 further includes an electronic control system 30 for controlling current flow to vary the temperature of each temperature-activated memory element 20 from a position external to the body so as to deflect the distal end 16 of the tubular member 12 in a plurality of different directions corresponding to the preset shapes of the elements 20. The control system 30 includes a power supply source 32 which may be either AC or DC. The system 30 also includes a control device 34 which, in the illustrative embodiment, is similar to a "joystick" control, tactile membrane switch, or ball controller. It will be appreciated that various types of control devices 34 may be employed without departing from the scope of the present invention.

The power supply source 32 is coupled through control device 34 to the tubular member 12 by cable 36 and a coupling device 38. Further, the temperature-activated memory elements 20 are electrically connected to the control device 34 through cable 36 and coupling 38 by electrical wires 40 which are attached to the body portions 22 of memory elements 20 by conventional means 42 such as soldering or crimping. Return or ground wires 44 are attached to the tip portions 24 of memory elements 20 by conventional means such as soldering or crimping 46. Return or ground wires 44 may be combined into a single ground cable 48 as shown in FIG. 2.

In the embodiment illustrated in FIG. 2, the temperature-activated memory elements 20 are carried on the exterior of the core 50 and ground wire 48 runs through the interior of the core 50. Core 50 couples each memory element 20 to at least one other memory element 20 so that when a memory element 20 moves to assume its preset shape in response to heat it applies a force to move the other memory element 20 coupled thereto. In preferred embodiments, the core 50 is a tube formed of urethane having a wall thickness of about 0.005 inch. In other embodiments, the core 50 may be a fiber optics bundle, electrical wire, microinstrumentation, or any other suitable member. Other mounting arrangements could be used for incorporating the memory elements 20 into the distal end 16 of the tubular member 12 without departing from the scope of the present invention.

In operation, the distal end 16 of the tubular member 12 is inserted into a body cavity 60 such as a blood vessel while memory elements 20 are straight and at a temperature below the transitional temperature. At this stage, each memory element 20 is in its second shape for ready insertion of the distal end 16 into the body cavity 60. The tubular member 12 is pushed through cavity 60 until it reaches a desired branch 62 or 64 extending from the cavity 60. Control device 34 is manipulated to apply an electrical voltage or current to one or more of the memory elements 20. Because of the high resistance of memory elements 20, heat is generated. When a memory element is heated to its predetermined transitional temperature (i.e., a predetermined temperature above body temperature) the memory element 20 moves to assume its preset shape (as shown by the broken lines in FIG. 3), thereby deflecting or moving the distal end 16 of tubular member 12 into one of the desired branch cavities 62 or 64. Once the distal end 16 is in the branch 62 or 64, power can be removed from the memory element 20 to allow it to cool. While the memory element 20 is at a temperature above its predetermined transitional temperature it remains relatively stiff in its preset shape. When the memory element 20 cools to a temperature below its predetermined transitional temperature it becomes soft or pliable in its preset shape. After cooling, a voltage or current is applied to another memory element 20 coupled to the cooled memory element 20 still in its preset shape. When the other memory element 20 reaches its predetermined transitional temperature, it begins to move to assume its preset shape and in doing so applies a force to the memory element 20 coupled thereto to move it to its second shape (as shown by the solid lines in FIG. 3). The catheter tubular member 12 can continue to be pushed through the branch 62 or 64 until it is again desirable to turn or bend the catheter 10.

As illustrated in FIG. 4, four temperature-activated memory elements 20 may be carried on the exterior of core 50. In the illustrative embodiment, pairs of the memory elements 20 are shown diametrically opposed to each other so that opposed elements 20 apply forces to each other when they are heated. Thus, the distal end 16 may be deflected in at least four different directions by applying an electrical current or voltage to one of the memory elements 20. It will be appreciated that more or less than four memory elements 20 may be utilized without departing from the scope of the present invention. However, it should be noted that at least two memory elements 20 are required. Further, it may be desirable to apply an electrical voltage or current to more than one of the memory elements 20 simultaneously to increase the number of directions in which the distal end 16 of the tubular member 12 may be deflected. The control system 30 may include means for regulating the application of current or voltage applied to the memory elements 20 to allow virtually an unlimited number of directions in which the distal end 16 may be deflected for the purpose of steering the catheter tubular member 10 through body cavities. It will be appreciated that a large number of wire memory elements could be incorporated into the distal end 16 and a voltage or current applied to one or more of the wires to deflect the distal end 16 in a desired direction.

Another application for a catheter 70 embodying the present invention is shown in FIGS. 5 and 6. Reference numerals from FIGS. 1-4 have been applied to the catheter 70 shown in FIGS. 5 and 6 where the same or similar parts are being used. Catheter 70 includes a tubular member 72 having a distal end 76. The distal end 76 includes a plurality of temperature-activated memory elements 20 of the type previously described. The same or similar control system may be employed in connection with the catheter 70 in a body cavity 80 for the purpose of aiming the distal end 76 at an obstruction, organ, or tissue 82 within the cavity 80. The catheter 70 may be anchored in the cavity 80 by a balloon 78. Once the catheter 70 is anchored, the distal end 76 is aimed in one of a plurality of directions to establish a course for the injection of fluid or a laser beam at the organ or tissue 82.

As shown in FIG. 6, a core 90 formed of insulative material passes through tubular member 72. Memory elements 20 are carried on the core 90 between the core 90 and the tubular member 72. Core 90 serves to couple each memory element 20 to at least one other memory element 20 in the manner and for the purpose previously described. The hollow core 90 may include a first tube 92 for carrying a fluid from the proximal end of the catheter 70 to the distal end 76. A return tube 94 may be included for extracting fluid. It will be appreciated that either passage 92 or 94 may be used for inserting a medical instrument into the cavity 80. Core 90 may also include a transparent member 95 providing a lens for observing the obstruction, organ, or tissue 82 and a bundle of fiber-optic lines 96 for transmitting light or a laser beam to the distal end 76. Thus, in the embodiment illustrated in FIGS. 5 and 6, catheter 70 has a distal end 76 which is aimable in a plurality of directions in accordance with the present invention for the purpose of establishing a course for the injection of fluid, light, or a laser beam at an obstruction, organ, or tissue 82.

Another embodiment of an arrangement for the memory elements 20 is shown in FIG. 7. The memory element arrangement 100 includes a plurality of memory elements 20 coupled at their distal ends 24 by a thermally and electrically insulative ring 102. Various materials, such as plastic, may be used to construct the ring 102. Ground wires from each memory element 20 are channeled through a common ground wire conduit 44. Ring 102 serves to couple the memory elements 20 to each other and performs a function similar to cores 50 and 90. This arrangement facilitates the mounting of the memory elements 20 in the distal end 16, 76 of the catheters 10, 70, respectively.

Yet another embodiment of the present invention is shown in FIGS. 8-11. Reference numerals from FIGS. 1-4 have been applied to a catheter 110 shown in FIGS. 8-11 where the same or similar parts are being used. Catheter 110 includes a tubular member 12, a pair of temperature-activated memory elements 20a and 20b, and a core 50 of the types described above. Memory elements 20a and 20b may be flat as shown in FIGS. 8-11 or in some applications may be wires, particularly where more than two memory elements are employed. The catheter 110 further includes a sleeve 112 for slidably coupling each memory element 20a, b to the core member 50 so that each memory element 20a, b is permitted to slip in relation to the adjacent core member 50 when at least one of the memory elements 20a, b moves to assume its predetermined shape. The sleeve 112 also interconnects one memory element to another memory element so that when one memory element moves in a first direction to assume its preset shape a force is applied to move the other memory element in the first direction and vice-versa.

Desirably, the sleeve 112 is a resilient tubular jacket for embracing elastically the core member 50 and the memory elements 20a,b to provide a slip interface therebetween. The sleeve 112 includes an axially inner portion 113 for the reception of a distal end of the core 50 and the tip portions 24 of each memory element and an axially outer portion 114 for the reception of a forward tip portion of the core. Thus, each memory element received within the sleeve 112 simultaneously is retainable in a core-guiding position as shown in FIGS. 9-11 and is movable with the sleeve 112 to deflect the distal end of the core 50 to a selected position (e.g. the deflected position illustrated in FIG. 11).

The sleeve 112 includes an inner wall 115 defining a slip chamber 116 in which each memory element is able to slip in relation to the core member 50 during selective heating of at least one of the memory elements 20. In preferred embodiments, the sleeve 112 is formed of thin MYLAR material having a thickness of about 0.001 inch. Any other similar material that has a low coefficient of friction and is not generally susceptible to deformation under heat would be suitable.

Figure 9:
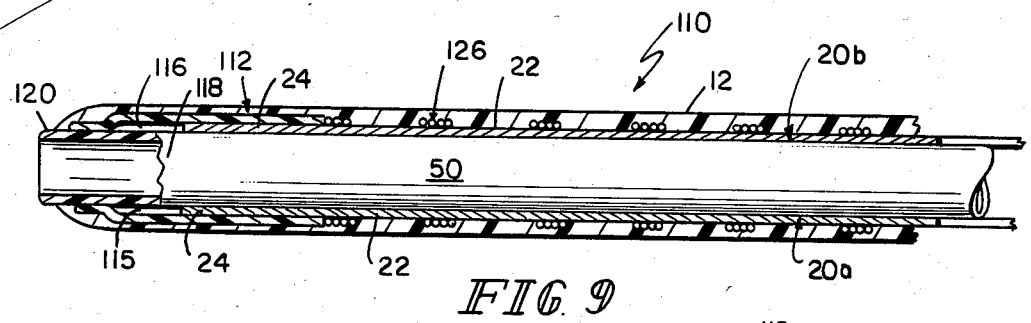
FIG. 9 is a longitudinal sectional view, partly broken away, showing the embodiment of FIG. 8 in its relaxed position and taken generally along section lines 9—9 of FIG. 8.

As shown best in FIGS. 8 and 9, the core 50 includes a distal end 118 having a forward tip portion 120. Installation of the sleeve 112 operates to position the forward tip portion 24 of each memory element 20a,b in close proximity to the distal end 118 of the core 50. The first and second memory elements 20a,b are positioned on opposite sides of the core 50 in spaced relation as shown in FIGS. 8, 9, and 11 so that the core 50 is intermediate the two memory elements. Thus, the forward tip portion 24 of each memory element is retained in its core-guiding position by sleeve 112. In addition, the remaining body portion 22 of each memory element is retained in its core-guiding position by means of a wrap.

Figure 10:
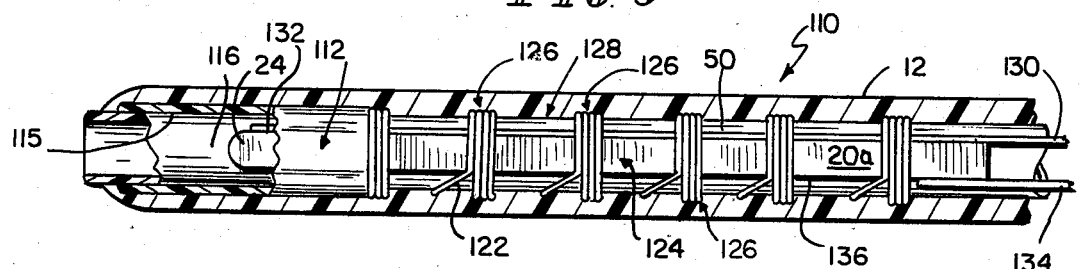
FIG. 10 is a view, partly broken away, of the embodiment of FIG. 9 rotated 90° about its longitudinal axis.
Figure 11:
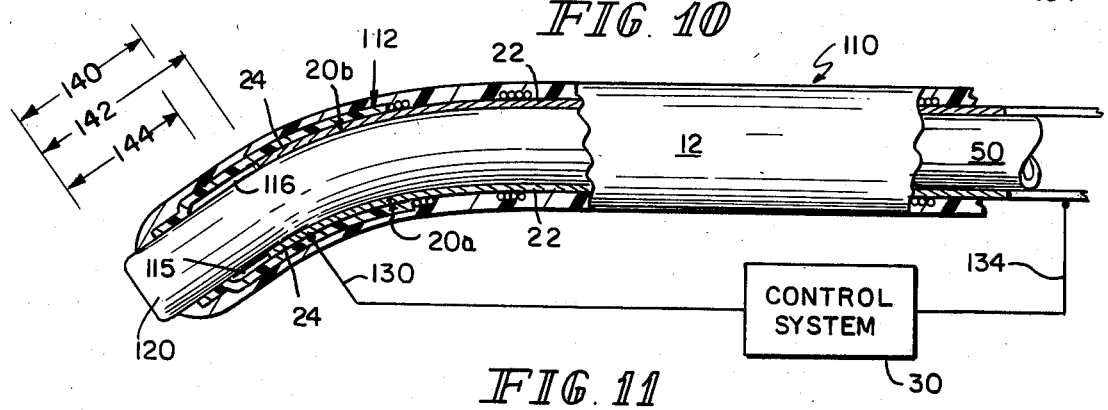
FIG. 11 is a longitudinal sectional view, partly broken away, showing the embodiment of FIG. 8 in a deflected position.

The memory element retaining wrap is desirably a continuous filament 122 as illustrated in FIGS. 8–11. For example, a nylon filament having a 0.002 inch diameter would be satisfactory. The filament wrap 122 couples at least a segment of the body portion 22 of each memory element 20a,b to the core 50 so that the body remaining portion segment is permitted to slip in relation to the adjacent core 50 when at least one of the memory elements 20a,b moves to assume its preset shape. Desirably, the filament wrap 122 embraces a radially outwardly-facing surface 124 of each of the memory elements in sufficiently tight relation to retain the memory elements in their coupled position while permitting relative slipping movement between each coupled memory element and the core 50. As shown in FIGS. 8 and 10, the continuous filament 122 defines a plurality of winding bunches 126 disposed along the length of the core 50 in spaced-apart relation so that each winding in a winding bunch 126 can move along the core in relation to one another in the spaces 128 therebetween during deflection or bending of the distal end 16 of the tubular member 12. Illustratively, each spaced winding bunch 126 includes three windings as shown in FIGS. 8 and 10.

In the embodiment illustrated in FIGS. 8–11, the temperature-activated memory elements 20a,b are electrically connected to the control device 34 by wire 130 of rectangular cross-section. The remainder of rectangular wire 130 is mounted along the side edge 132 of the remaining portion 22 of each memory element 20. Return or ground wire 134 is also of rectangular cross-section and mounted along another side edge 136 of each memory element at a proximal end of the remaining body portion 22 of the memory element. Other suitable electrical coupling means are usable to couple the memory elements of the embodiment of FIGS. 8–11 to the control device 34 without departing from the scope of the present invention.

In operation, the sleeve 112 included in the embodiment of FIGS. 8–11 provides numerous advantages. One advantage is that maneuverability of the catheter 110 is improved due to slippage of each memory element 20a,b relative to core 50 in the slip chamber 116 defined by the sleeve 112. A certain amount of slippage is desirable to allow relative movement of the memory elements 20 and the core 50 to improve the flexibility of the catheter. As shown best in FIG. 11, movement of the first memory element 20a to assume its predetermined position causes the forward tip portion 24 of the first memory element 20a to move along the exterior surface of the core 50 toward the forward tip portion 120 of the core 50 and the forward tip portion 24 of the second memory element 20b to move along the exterior surface of the core 50 away from the forward tip portion 120 of the core 50. In other words, the first memory element 20b is arcuately shaped when the memory element 20a moves to assume its predetermined shape and vice versa. In particular, the arc defined by the memory element 20a is smaller than the arc defined by the equidistantly spaced-apart memory element 20b as shown in FIG. 11. The slippage of memory elements 20a and 20b relative to the forward tip portion 120 of core 50 is shown by the arrows in FIG. 11. Arrow 140 represents the positions of the tips 24 before deflection and arrows 142 and 144 represent the positions of the tips 24 of elements 20b and 20a respectively when the catheter is deflected.

While illustrative embodiments and uses of catheters, cannulae, and the like embodying the present invention have been shown and described, it will be appreciated that various modifications may be made to the illustrative embodiments without departing from the scope of the present invention.

What is claimed is:

1. A catheter comprising
   an elongated hollow tubular member having a proximal end and a distal end for insertion into the body,
   a core member within the distal end of the hollow tubular member,
   at least two temperature-activated memory elements within the distal end of the hollow tubular member, each memory element moving to assume a predetermined shape when heated to a predetermined temperature,
   coupling means for coupling one memory element to another memory element so that when the one memory element moves in a first direction to assume its predetermined shape a force is applied to move the other memory element in the first direction and when the other memory element moves in a second direction to assume its predetermined shape a force is applied to move the one memory element in the second direction, the coupling means including sleeve means for slidably coupling each memory element to the core member so that each memory element is permitted to slip in relation to the adjacent core member when at least one of the memory elements moves to assume its predetermined shape, and
   control means for selectively heating each memory element to move at least one of the memory elements to assume its predetermined shape to deflect the distal end of the tubular member in a selected direction and to slide each memory element in relation to the adjacent core member so that the memory elements are able to move in slipping relation to the distal end of the core member, whereby maneuverability of the tubular member within the body toward a selected deflected position is increased.

2. The catheter of claim 1, wherein the sleeve means is a resilient tubular jacket for embracing the core member and the memory elements, the tubular jacket having an inner wall defining a slip chamber in which each memory element is able to slip in relation to the core member during selective heating of at least one of the memory elements.

3. The catheter of claim 1, wherein first and second memory elements are coupled to the core member, and the first memory element has a first radius of curvature and the second memory element has a second radius of curvature that is greater than the first radius of curvature when the first memory element moves to assume its predetermined shape.

4. The catheter of claim 1, each memory element includes a tip portion and a body portion and the coupling means further includes wrap means for slidably coupling at least a segment of the body portion of the core member so that the body portion segment is permitted to slip in relation to the core member when at least one of the memory elements moves to assume its predetermined shape.

5. The catheter of claim 1, wherein the core member includes a distal end positioned within the distal end of the hollow tubular member and the sleeve means couples each memory element to the distal end of the core member.

6. The catheter of claim 5, wherein each memory element includes a tip portion and a body portion, and the sleeve means is a tubular jacket including an axially inner sleeve portion for the reception of the distal end of the core member and the tip portions of each memory element and an axially outer sleeve portion for the reception of the distal end of the core member.

7. The catheter of claim 6, wherein the tubular jacket is formed of a resilient material to embrace elastically the received memory elements so that each received memory element both is retainable in a core-guiding position and movable within the resilient tubular jacket to guide the distal end of the core to a selected position.

8. The catheter of claim 7, wherein the core and the tubular member are interconnected so that guided movement of the core in response to operation of at least one memory element moves the tubular member to a selected deflected position.

9. The catheter of claim 5, wherein the distal end of the core member has a forward tip portion, each memory element has a forward tip portion in close proximity to the distal end of the core member, first and second memory elements are positioned on opposite sides of the core member in spaced relation so that the core member is intermediate the first and second memory elements, and movement of the first memory element to assume its predetermined position causes the forward tip portion of the first memory element to move toward the forward tip portion of the core member and the forward tip portion of the second memory element to move away from the forward tip portion of the core member.

10. A catheter comprising
an elongated hollow tubular member having a proximal end and a distal end for insertion into the body,
a core member having a distal end positioned within the distal end of the hollow tubular member and movable therein,
at least two temperature-activated memory elements within the distal end of the hollow tubular member, each memory element having a tip portion and a body portion and moving to assume a predetermined shape when heated to a predetermined temperature,
sleeve means for slidably coupling the tip portion of each memory element to the distal end of the core member so that the tip portion of each memory element is permitted to slip in relation to the adjacent core member when at least one of the memory elements moves to assume its predetermined shape,
wrap means for slidably coupling at least a segment of the body portion to the core member so that the body portion segment is permitted to slip in relation to the adjacent core member when at least one of the memory elements moves to assume its predetermined shape, and
control means for selectively heating each memory element to move at least one of the elements to assume its predetermined shape to deflect the distal end of the tubular member in a selected direction and to slide the tip portion and the body portion segment of each memory element in relation to the adjacent core member so that the memory elements are able to move in slipping relation to the core member, whereby maneuverability of the tubular member within the body toward a selected deflected position is increased.

11. The catheter of claim 10, wherein the wrap means is a continuous filament.

12. The catheter of claim 11, wherein the filament embraces a radially outwardly-facing surface of each of the memory elements in sufficiently tight relation to retain the memory elements in their coupled position while permitting relative slipping movement between each coupled memory element and the core member.

13. The catheter of claim 10, wherein the continuous filament defines a plurality of winding bunches disposed along the length of the core member in spaced-apart relation so that the windings can move along the core member in relation to one another in the spaces therebetween during deflection of the distal end of the tubular member.

14. The catheter of claim 13, wherein each winding bunch includes three filament windings.

15. A catheter comprising
an elongated hollow tubular member having a proximal end and a distal end for insertion into the body,
a core member having a distal end positioned within the distal end of the hollow tubular member and movable therein,
at least two temperature-activated memory elements within the distal end of the hollow tubular member, each memory element assuming a predetermined shape when heated to a predetermined temperature,
sleeve means for slidably coupling each memory element to the distal end of the core member so that each memory element is permitted to slip in relation to the adjacent core member when at least one of the memory elements moves to assume its predetermined shape and for coupling one memory element to another memory element so that when the one memory element moves in a first direction to assume its predetermined shape a force is applied to move the other memory element in the first direction and when the other memory element moves in a second direction to assume its predetermined shape a force is applied to move the one memory element in the second direction, and
control means for selectively heating each memory element so that each memory element slides in relation to the adjacent core member, the one memory element is moved to deflect the distal end of the tubular member in the second direction when the other memory element is heated to assume its predetermined shape, and the other memory element is moved to deflect the distal end of the tubular member in the first direction when the one memory element is heated to assume its predetermined shape, whereby maneuverability of the tubular member within the body toward a selected deflected position is increased.

* * * * *